United States Patent
Jackson et al.

(10) Patent No.: US 12,258,802 B1
(45) Date of Patent: Mar. 25, 2025

(54) DOOR HINGE FOR FLOAT POD

(71) Applicant: True Rest Franchising, LLC, Coronado, CA (US)

(72) Inventors: Mark A Jackson, Clovis, CA (US); Abraham Kezirian, Fresno, CA (US); Shaun Cuaron, Clovis, CA (US)

(73) Assignee: True REST Franchising, LLC, Coronado, CA (US)

( * ) Notice: Subject to any disclaimer, the term of this patent is extended or adjusted under 35 U.S.C. 154(b) by 932 days.

(21) Appl. No.: 17/367,748

(22) Filed: Jul. 6, 2021

(51) Int. Cl.
| E05D 11/06 | (2006.01) |
| A61M 21/00 | (2006.01) |
| E05D 3/04 | (2006.01) |
| E05D 5/04 | (2006.01) |
| E05D 5/10 | (2006.01) |
| E06B 5/00 | (2006.01) |

(52) U.S. Cl.
CPC ........... *E05D 3/04* (2013.01); *A61M 21/0094* (2013.01); *E05D 5/04* (2013.01); *E05D 5/10* (2013.01); *E06B 5/00* (2013.01); *E05D 2005/104* (2013.01); *E05Y 2999/00* (2024.05)

(58) Field of Classification Search
CPC .... E05D 3/04; E05D 5/04; E05D 5/06; E05D 5/10; E05D 5/12; E05D 2005/104; A61M 21/0094; E06B 5/00; E05Y 2999/00; E05Y 16/365; E05Y 16/387; E05Y 16/389; E05Y 16/39; E05Y 16/273; E05Y 16/275; E05Y 16/276
See application file for complete search history.

(56) References Cited

U.S. PATENT DOCUMENTS

| 1,752,428 | A | * | 4/1930 | Farver | ..................... E05D 7/081 16/365 |
| 2,261,658 | A | * | 11/1941 | Mulchay | ................. D06F 57/04 211/165 |
| 2,728,115 | A | * | 12/1955 | Cornelius | ............. E04B 1/3448 160/39 |
| 3,626,547 | A | * | 12/1971 | Werner | ................... E05D 11/04 16/314 |
| 4,246,663 | A | * | 1/1981 | Aragona | ................. E04H 3/165 4/534 |
| 4,566,475 | A | * | 1/1986 | Wund | ..................... E04H 3/165 52/65 |

(Continued)

FOREIGN PATENT DOCUMENTS

| DE | 2400993 | A1 | * | 7/1975 |
| FR | 2719618 | B1 | * | 7/1996 |
| GB | 1123791 | A | * | 8/1968 |

*Primary Examiner* — Chuck Y Mah
(74) *Attorney, Agent, or Firm* — Symbus Law Group PLLC; Craig A. Simmermon

(57) ABSTRACT

Systems, devices, and methods for operating one or more doors of an enclosure from an open position to a closed position are disclosed. In particular, the present disclosure relates to the opening and closing of a pair of curved double-doors of a float pod. Such opening and closing is achieved via a door hinge attached to the float pod. In some embodiments, the door hinge includes two arms that rotate independently around a central, pivoting shaft. Each of the pair of curved double-doors is attached to one of the two arms, thereby resulting in lateral, sliding movement of the doors towards and away from each other upon rotation of the two arms.

14 Claims, 11 Drawing Sheets

(56) References Cited

U.S. PATENT DOCUMENTS

| | | | | |
|---|---|---|---|---|
| 5,449,073 | A * | 9/1995 | DeBeverly | A47F 7/00 |
| | | | | 211/85.2 |
| 5,625,982 | A * | 5/1997 | Foote | E04B 1/3211 |
| | | | | 52/64 |
| 5,740,828 | A * | 4/1998 | Evans | E04H 6/04 |
| | | | | 135/132 |
| 6,052,951 | A * | 4/2000 | Daoud | E04B 1/3448 |
| | | | | 52/64 |
| 6,206,210 | B1 * | 3/2001 | Reed | A47F 5/0087 |
| | | | | 211/96 |
| 8,944,300 | B1 * | 2/2015 | Kaufman | A45B 11/02 |
| | | | | 224/628 |
| 2006/0219279 | A1 * | 10/2006 | Kaufman | A45B 11/02 |
| | | | | 135/33.71 |
| 2007/0028530 | A1 * | 2/2007 | De Laporte | E04B 1/3448 |
| | | | | 52/66 |
| 2012/0247034 | A1 * | 10/2012 | Wystup | E04H 3/165 |
| | | | | 52/65 |

* cited by examiner

DOOR HINGE FOR FLOAT POD

FIELD OF THE DISCLOSURE

This disclosure relates generally to controlling the opening, closing, and movement of one or more doors on an enclosure. Specifically, the disclosure relates to a door hinge for operating a set of two doors on a float pod or isolation tank, where the hinge operates the doors by moving them laterally towards and away from each other.

BACKGROUND

Existing methods for opening and closing curved and/or sliding doors require one or more lifting mechanisms, such as hydraulic pumps or pistons. For instance, float pods (often alternatively called "isolation tanks" or "sensory deprivation tanks") often have large curved doors to permit the user access into the pod. However, known, commercially-available opening and closing mechanisms suitable for the doors of such float pods require an oval shape and hydraulic pistons for opening the doors vertically, similar to the opening of a trapdoor or other sliding or hinged door.

Needs therefore exist for improved door hinges for curved and/or sliding doors that eliminate the need for any hydraulic piston or other lifting mechanism.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description. Rather, the scope of the invention is defined by the appended claims.

In certain embodiments, the disclosed embodiments may include one or more of the features described herein.

The present disclosure in various embodiments relates to the movement of one or more doors of an enclosure, e.g., between an open position and a closed position. Specifically, embodiments include a system for opening and closing one or more doors of an enclosure, comprising the enclosure (which can be, for instance, a float pod), a door hinge affixed to the enclosure, and one or more doors affixed to one or more portions of the door hinge such that movement of the one or more portions move the one or more doors laterally towards and away from each other in a sliding fashion, thereby opening and closing an entrance to the enclosure.

Thus, embodiments of the disclosure enable the opening and closing of doors of a float pod so that entrance to the float pod is effected easily and so that the float pod doors effectively close and remain close while a user is inside, thereby ensuring a dark environment and a lack of sensory stimulation.

Embodiments of the present disclosure include a hinge able to open a door (such as, for instance, a curved and/or sliding door) via sliding. The hinge therefore does not require a hydraulic piston or other such lifting mechanism. In at least one embodiment, the hinge enables the door to open laterally, rather than vertically, as would be the case with a hydraulic piston.

In one or more embodiments, the hinge comprises an independently pivoting structure, the structure comprising at least two pivoting arms, a central pivoting shaft, and a single axle, all of which are mounted to a rigid base plate. Each of the two pivoting arms may be affixed to, or part of, a door. During operation, the two pivoting arms move towards and away from each other, thereby opening and closing the doors.

The hinge may be made of, for instance, steel, aluminum, and/or alloys thereof (e.g., 6061 aluminum alloy, 7075 aluminum alloy). These hinge materials may either independently, or in combination with the arm geometry and/or position of the arms relative to each other and/or relative to the axle or plate, permit the support of independent cantilever loads (e.g., one or more doors, including a set of double doors) with minimal arm deflection.

In at least an additional embodiment, one or more surfaces of the at least two pivoting arms impact each other at one or more points during the operation of the hinge, and further limit the maximum angle or degree of opening between each of the at least two arms to 180 degrees.

Therefore, one or more embodiments of the hinge described therein can be used to open curved doors in a sliding, lateral fashion, such as, for instance, curved doors present in a float pod, isolation tank, sensory deprivation tank, or the like.

These and further and other objects and features are apparent in the disclosure, which includes the above and ongoing written specification, with the drawings.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein.

DETAILED DESCRIPTION

Figure 1:
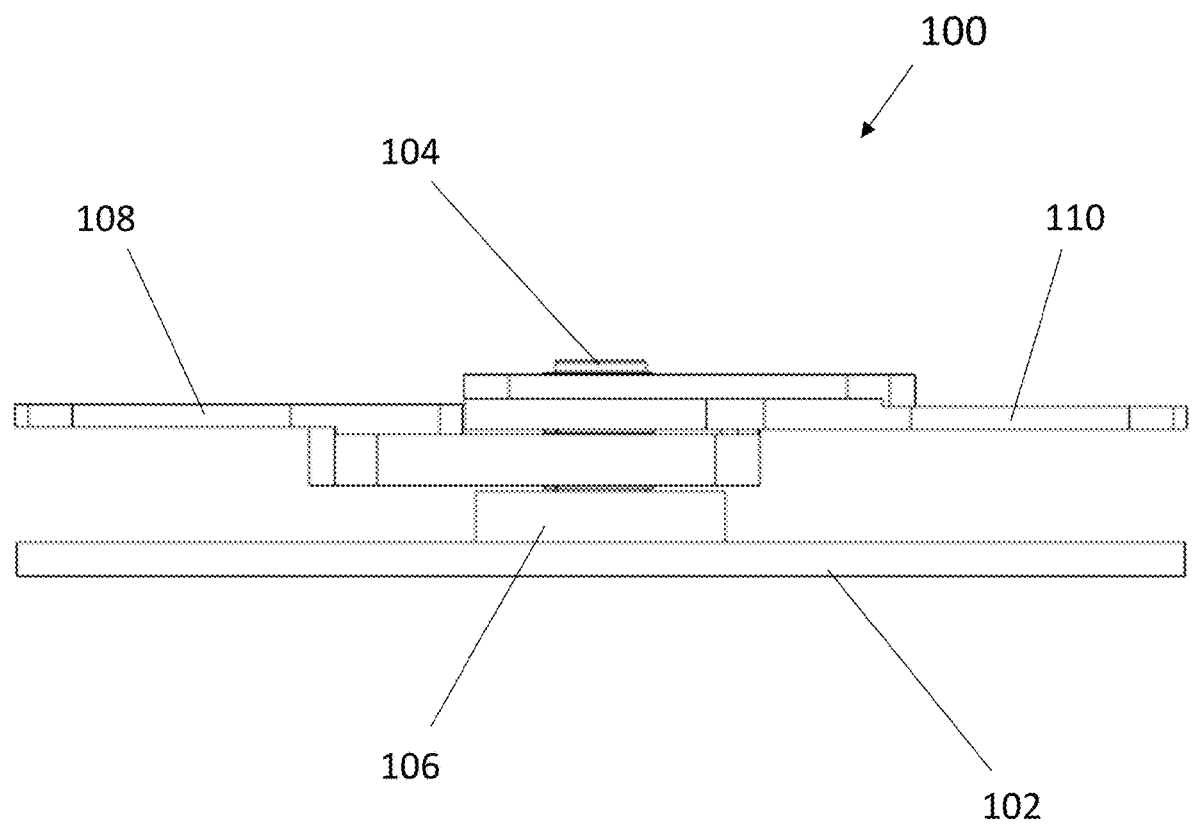
FIG. 1 is a schematic diagram of a side view of a hinge, according to an example embodiment.

A door hinge will now be disclosed in terms of various exemplary embodiments. This specification discloses one or more embodiments that incorporate features of the invention.

The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

In the several figures, like reference numerals may be used for like elements having like functions even in different drawings. The embodiments described, and their detailed construction and elements, are merely provided to assist in a comprehensive understanding. Thus, it is apparent that the present invention can be carried out in a variety of ways, and does not require any of the specific features described herein. Also, well-known functions or constructions are not described in detail since they would obscure the disclosure with unnecessary detail. Any signal arrows in the drawings/figures should be considered only as exemplary, and not limiting, unless otherwise specifically noted.

The description is not to be taken in a limiting sense, but is made merely for the purpose of illustrating the general principles, since the scope of the invention is best defined by the appended claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items. As used herein, "at least one of A, B, and C" indicates A or B or C or any combination thereof. As used herein, the singular form of a word includes the plural, and vice versa, unless the context clearly dictates otherwise. Thus, the references "a", "an", and "the" are generally inclusive of the plurals of the respective terms.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

As used herein, ranges are used herein in shorthand, so as to avoid having to list and describe each and every value within the range. Any appropriate value within the range can be selected, where appropriate, as the upper value, lower value, or the terminus of the range.

The words "comprise," "comprises," and "comprising" are to be interpreted inclusively rather than exclusively. Likewise, the terms "include," "including," and "or" should all be construed to be inclusive, unless such a construction is clearly prohibited from the context. The terms "comprising" or "including" are intended to include embodiments encompassed by the terms "consisting essentially of" and "consisting of." Similarly, the term "consisting essentially of" is intended to include embodiments encompassed by the term "consisting of." Although having distinct meanings, the terms "comprising," "having," "containing," and "consisting of" may be replaced with one another throughout the description of the invention.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

"About" means a referenced numeric indication plus or minus 10% of that referenced numeric indication. For example, the term "about 4" would include a range of 3.6 to 4.4. All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims, each numerical parameter should be construed in light of the number of significant digits and ordinary rounding approaches.

Wherever the phrase "for example," "such as," "including" and the like are used herein, the phrase "and without limitation" is understood to follow unless explicitly stated otherwise.

"Typically" or "optionally" means that the subsequently described event or circumstance may or may not occur, and that the description includes instances where said event or circumstance occurs and instances where it does not.

Generally, the disclosure relates to devices, systems, and methods for opening and closing one or more doors of an enclosure (such as, for instance, a float pod), thereby ensuring darkness inside the enclosure. It should be appreciated that such darkness is critical for operation of a float pod or isolation tank, since it provides a reduced sensory environment that can be used as a form of therapy for users.

Accordingly, embodiments of the disclosure relate to a system that includes an enclosure such as a float pod, a door hinge attached to the enclosure, and one or more doors of the enclosure that are connected to one or more portions of the door hinge. In certain embodiments, the hinge may comprise one or more arms that rotate about a central pivoting shaft, with each of the one or more arms affixed to a door of the enclosure such that rotation of an arm results in lateral movement of the corresponding door. The hinge may, in some embodiments, be affixed to a pair of curved double-doors that, in operation, slides the two portions of the double-doors away from each other for opening, and towards each other for closing.

In at least one embodiment, the hinge opens the one or more doors laterally, rather than vertically. Therefore, it should be appreciated that the hinge operates to open the one or more doors without the need for a hydraulic piston, pump, or other lifting mechanism. It should be further appreciated that the hinge opens the one or more doors laterally as opposed to vertically (such as how a trapdoor or hinged door opens).

At least one or more embodiments disclosed herein may be used to open and close doors in a sliding fashion, such as, for instance, the doors of a float pod. As used herein, the term "float pod" is synonymous with other terms such as, for instance, "isolation tank," "sensory deprivation tank," "float tank," "flotation tank," "float cabin," "sensory attenuation tank," or the like. A skilled artisan will appreciate that such float pods are generally enclosed spaces or environments with one or more doors that can be opened and closed to permit a user access into the interior of the pod. Float pods often have various features in common, including, but not limited to, a lack of sound, a lack of visible light, and/or an interior that is heated to a comfortable temperature (e.g., body temperature). The float pod further comprises a small amount of water (e.g., a foot or less in depth) with one or more types of salts (e.g., Epsom salts) that enable a user to float in the water. The specific gravity of the water thus may be in the range of approximately 1.25-1.26.

Float pods may be soundproof and/or completely dark with respect to visible light. Thus, a user floating in the water inside a float pod experiences a lack of sensory stimulation and an observable environment. Float pods can therefore be used as a form of reduced environment stipulation therapy (REST), which can help float pod users with visualization techniques, anxiety disorders, overstimulation, and stress.

Turning now to FIG. 1, a side view of a door hinge is shown. The hinge 100 comprises a base plate (also referred to herein as a "base") 102 on which a central, pivoting shaft 104 is connected. The shaft 104 is connected to the base 102 through a shaft support 106. Attached vertically above the shaft support are two pivoting arms 108 and 110. The pivoting arms are therefore attached on the pivoting shaft 104 and can rotate laterally (i.e., in a horizontal plane) with respect to the shaft, the shaft support, and the base. Each of the pivoting arms 108 and 110 are able to rotate around the shaft 104 independently of each other.

Figure 2:
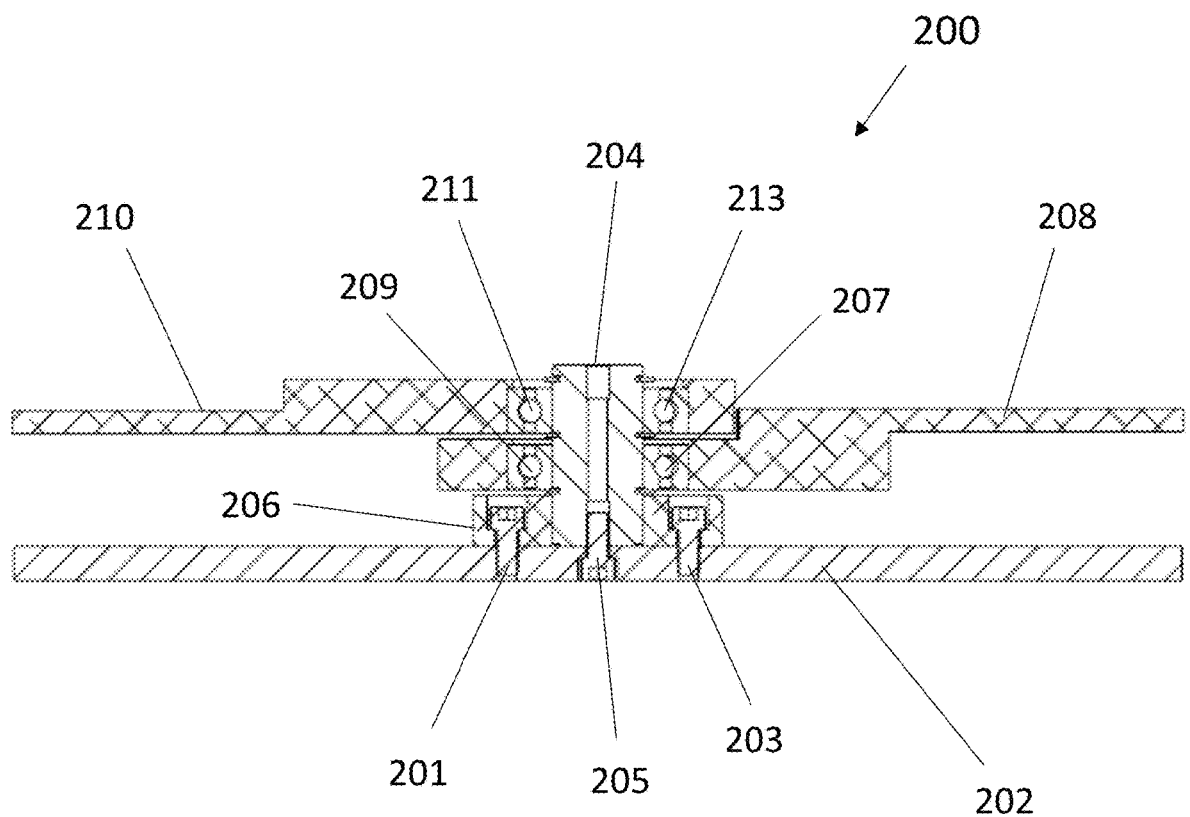
FIG. 2 is another schematic diagram of a side view of a hinge, according to an example embodiment.

FIG. 2 provides a further side view of a hinge 200. As in FIG. 1, a central, pivoting shaft 204 is connected to a base plate 202 via a shaft support 206. The shaft support 206 is connected to the base via two screws 201 and 203, one on each side of the shaft 204. Additionally, the shaft 204 is connected to the base via a screw 205.

Two pivoting arms 208 and 210 are affixed to the pivoting shaft 204 vertically above the shaft support 206. Both of the pivoting arms rotate laterally (i.e., in a horizontal plane) with respect to the pivoting shaft. Further, the pivoting arms rotate independently with respect to each other. Pivoting arm 208 is connected to the pivoting shaft at least via bearings 207 and 209. Similarly, pivoting arm 210 is connected to the pivoting shaft at least via bearings 211 and 213.

Figure 3:
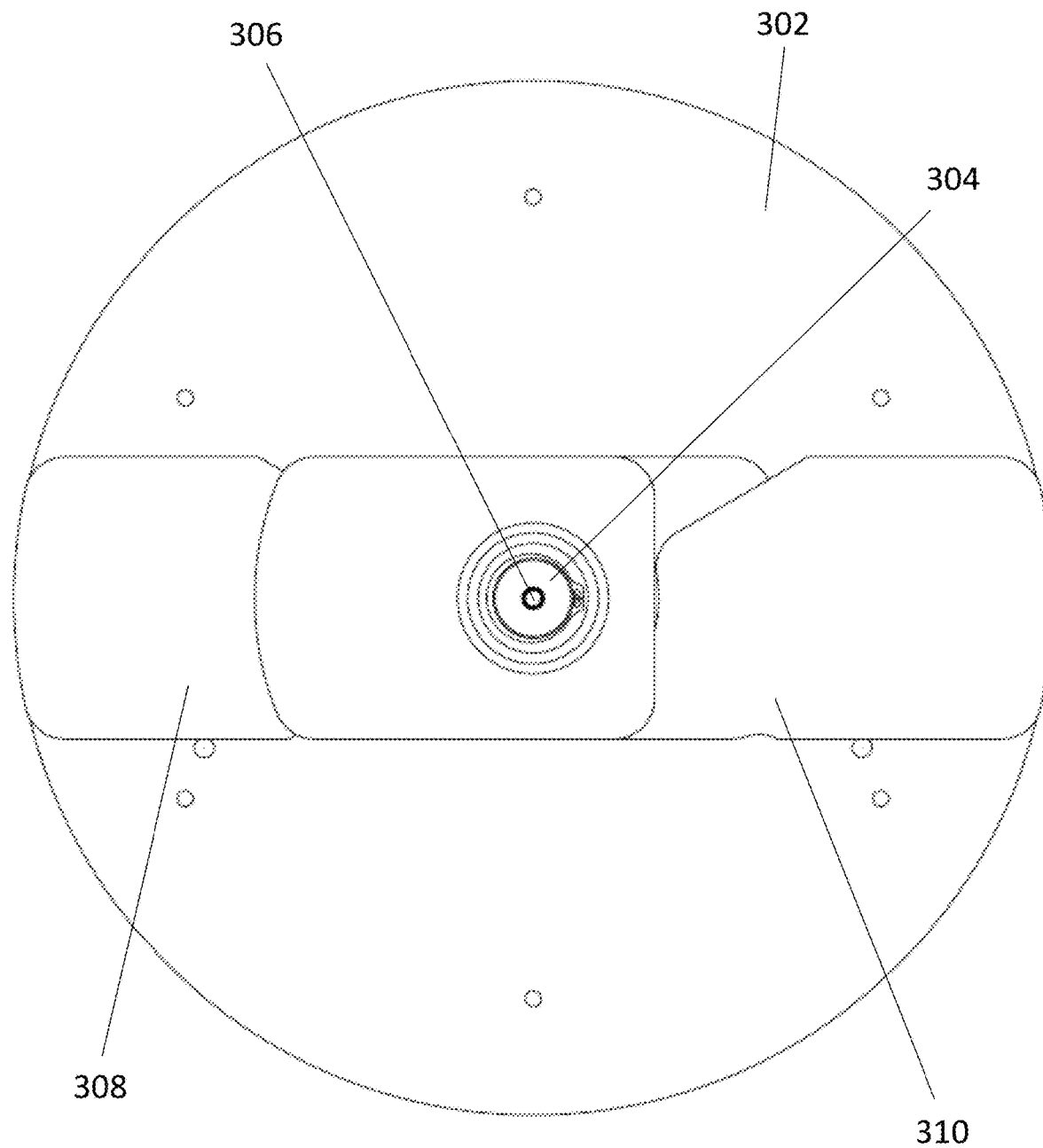
FIG. 3 is a schematic diagram of a top-down view of a hinge operable to move two doors of an enclosure, with the doors in an open position, according to an example embodiment.

As stated previously herein, the hinge may, in at least one embodiment, control the movement of one or more doors, e.g., a pair of double doors. Turning now to FIG. 3, a top down view of an enclosure 302 is shown. This enclosure 302 may be, for instance, a float pod. The hinge 304 is affixed to the enclosure, and comprises a central pivoting shaft 306 on which at least two rotating arms (not shown) rotate. Each of the at least two rotating arms is connected to doors 308 and 310. Thus, it should be appreciated that one rotating arm is affixed to, and controls the movement of, door 308, while another rotating arm is affixed to, and controls the movement of, door 310.

As shown in FIG. 3, door 308 extends laterally to the left of the hinge, while door 310 extends laterally to the right of the hinge. Thus, the doors 308 and 310 are one-hundred and eighty degrees apart from each other. In this position, both doors are in an open position, thereby permitting entrance (not shown) to the enclosure.

Figure 4:
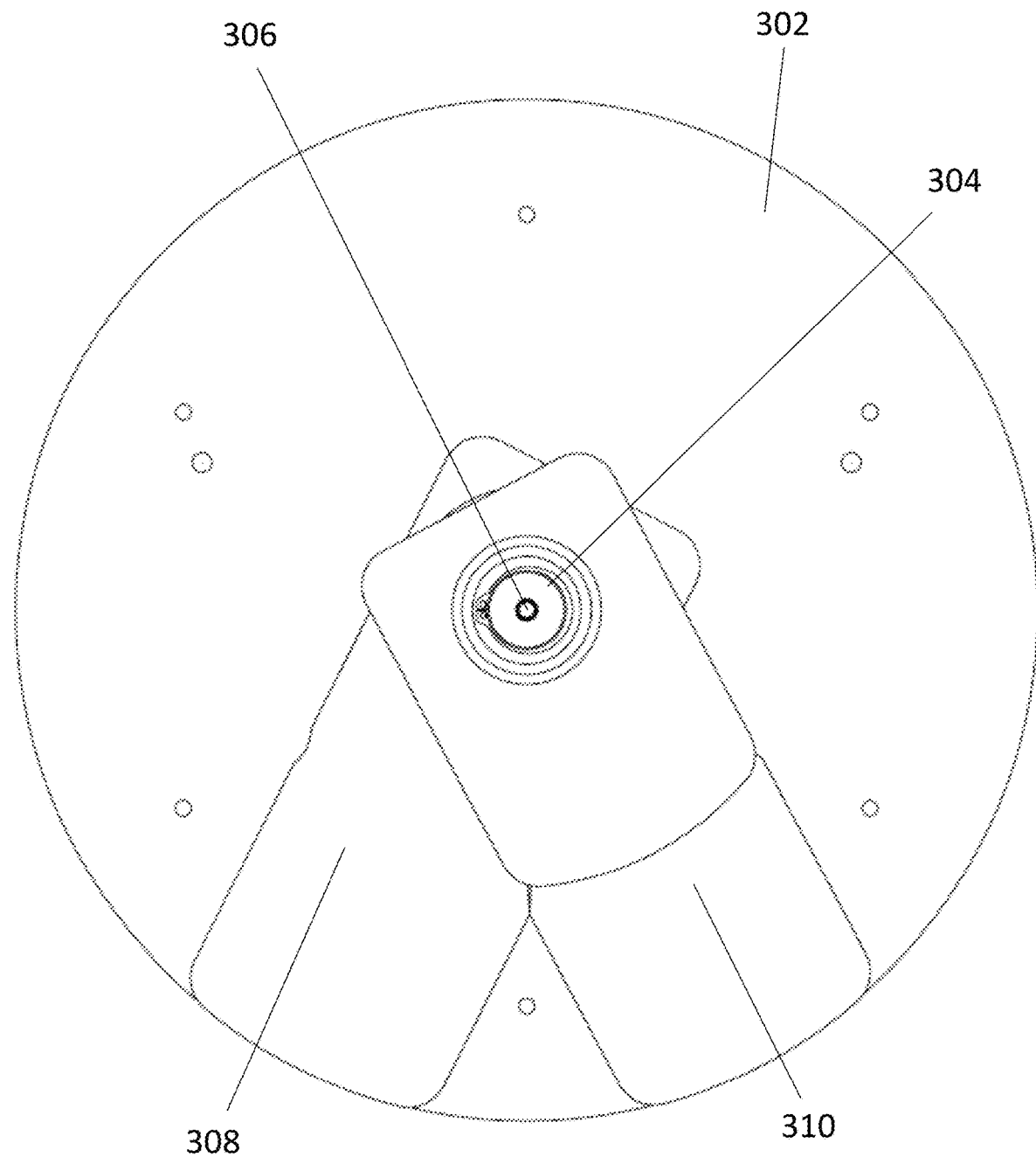
FIG. 4 is another schematic diagram of a top-down view of a hinge operable to move two doors of an enclosure, with the doors in a closed position, according to an example embodiment.

FIG. 4 shows an additional top down view of the same enclosure 302, with the same hinge 304 and doors 308, 310. However, the doors 308, 310 are shown herein in a closed position, with each door having rotated towards the other. Thus, the angle between the doors 308, 310 is less than one-hundred and eighty degrees apart. It should be appreciated that the doors may be in a closed position when they contact each other.

Movement of the doors 308, 310 into the closed position is achieved by the hinge 304, and specifically by the movement of the two rotating arms (not shown) of the hinge, with each rotating arm being affixed to each of the doors. Each rotating arm rotates independently around the pivoting shaft 306.

Figure 5:
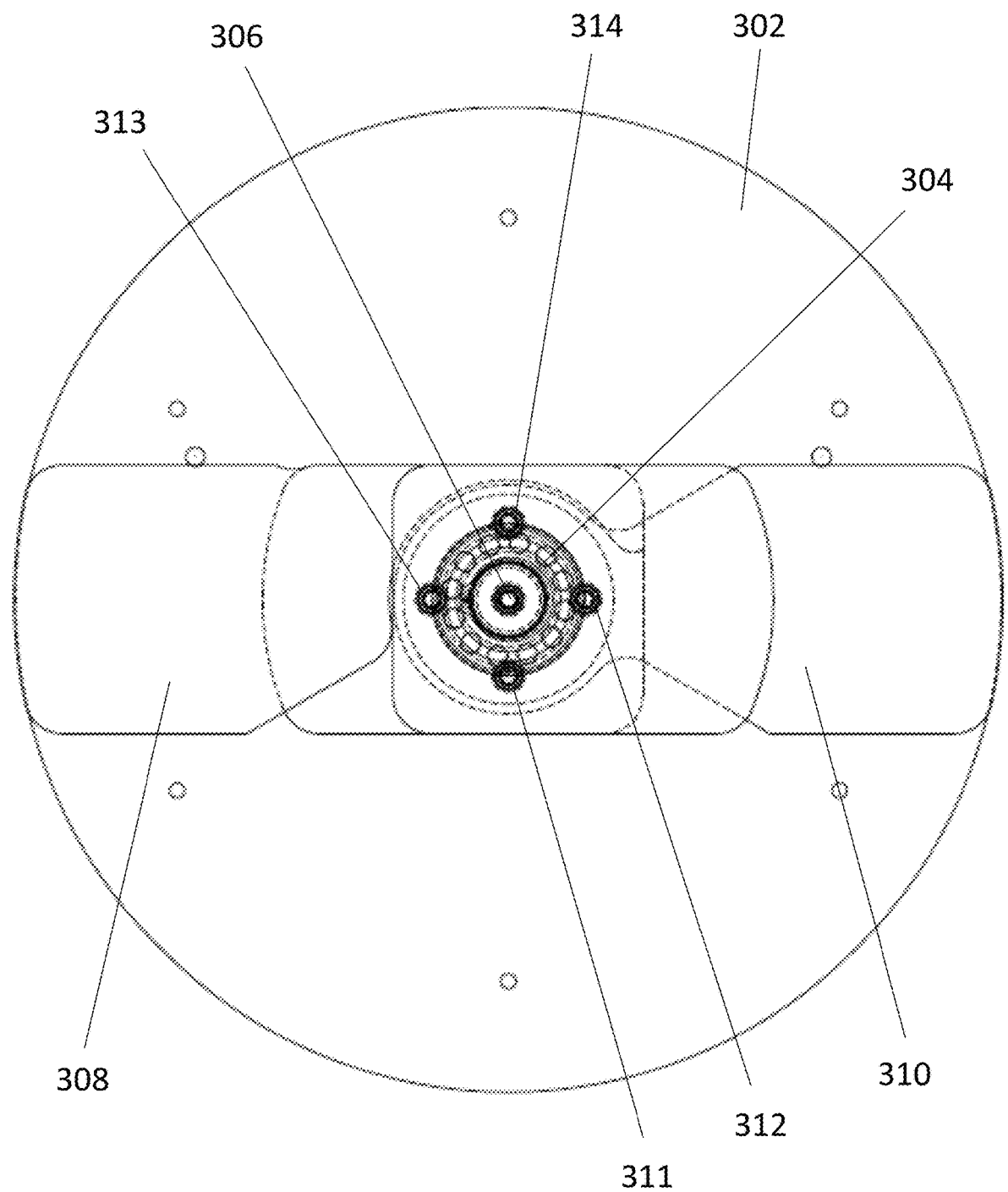
FIG. 5 is a schematic diagram of a top-down view of a hinge operable to move two doors of an enclosure, with the doors in an open position, according to an example embodiment.
Figure 6:
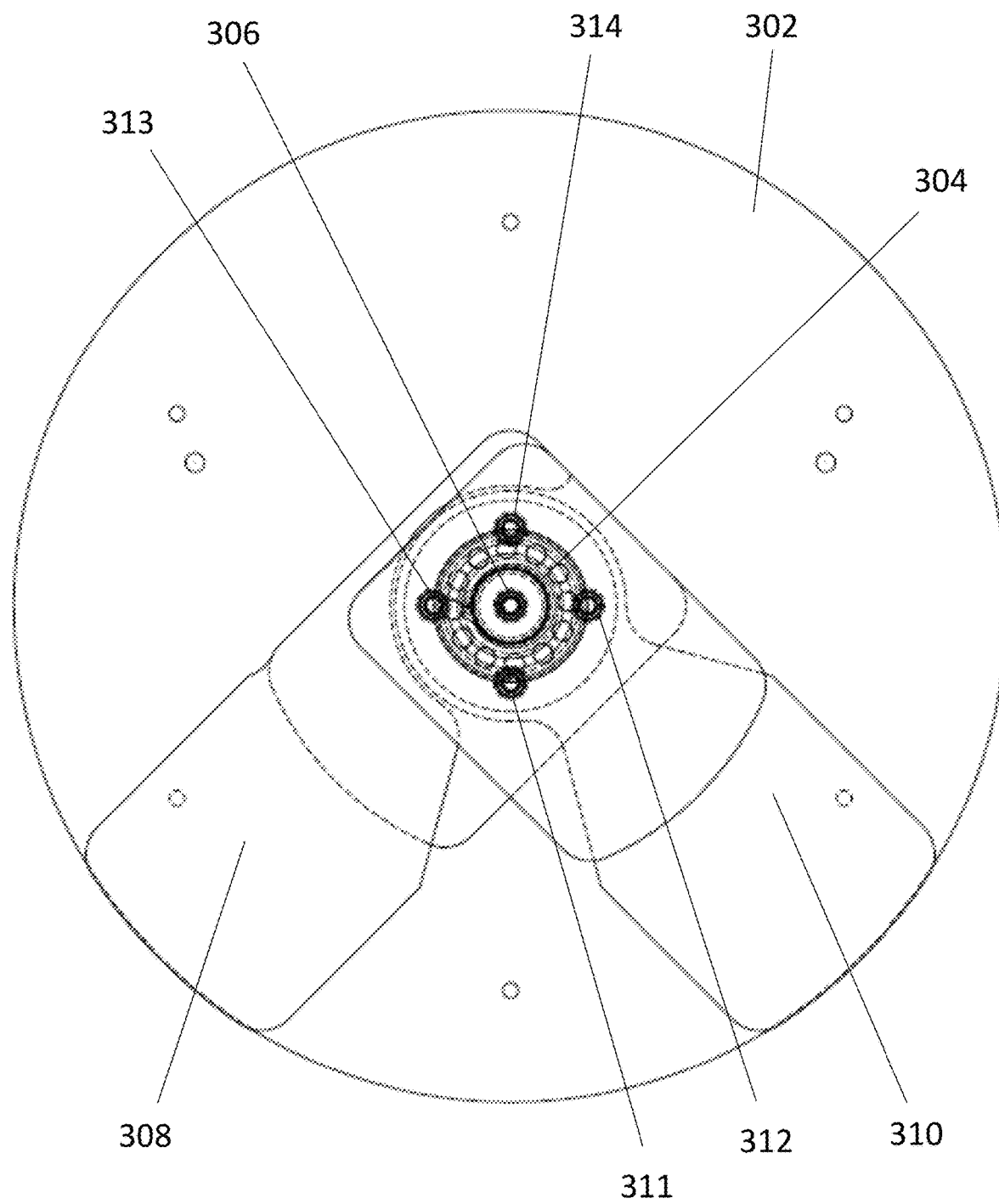
FIG. 6 is another schematic diagram of a top-down view of a hinge operable to move two doors of an enclosure, with the doors in a position partially between an open and a closed position, according to an example embodiment.
Figure 7:
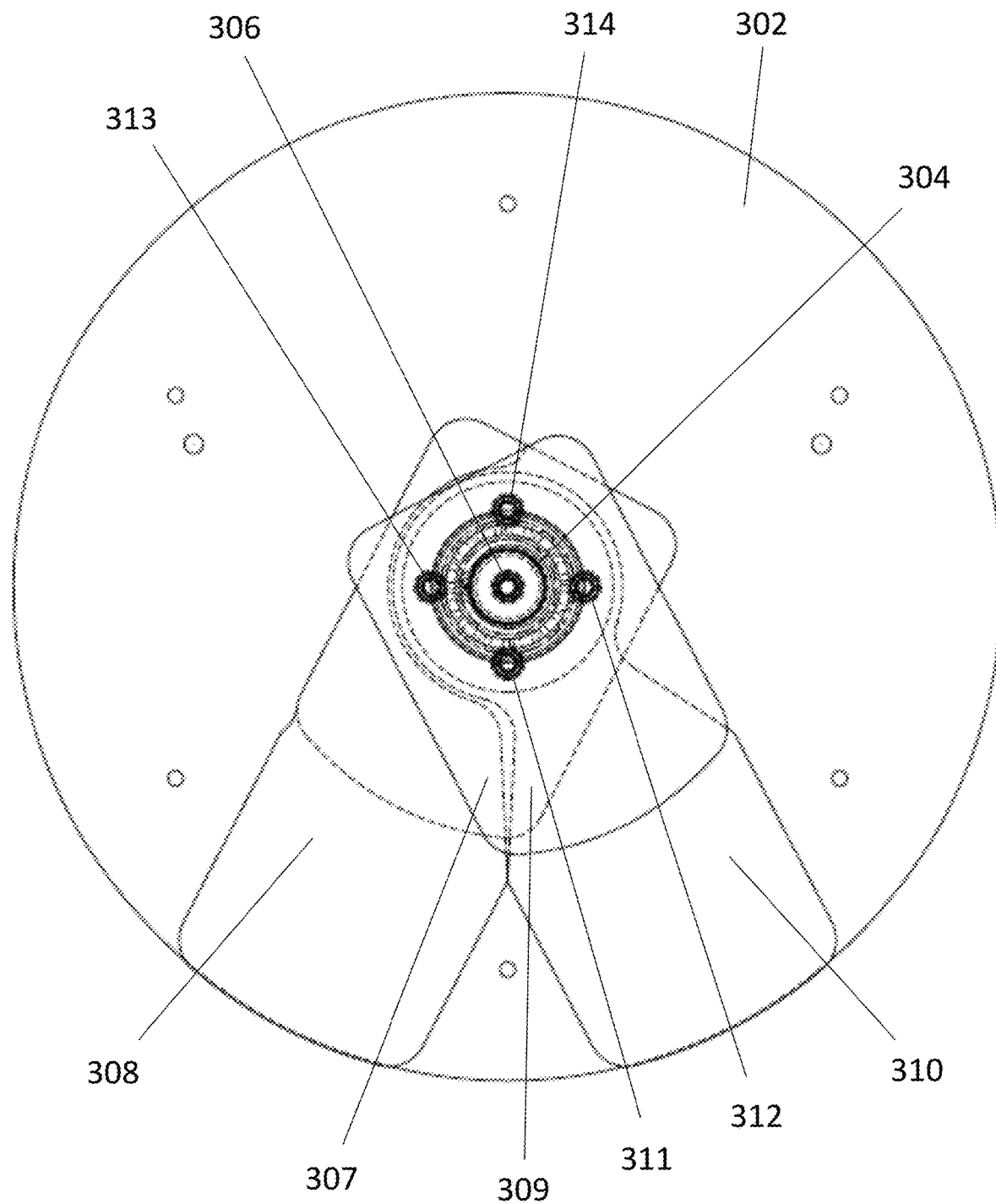
FIG. 7 is a further schematic diagram of a top-down view of a hinge operable to move two doors of an enclosure, with the doors in a closed position, according to an example embodiment.

Further illustration of the enclosure and doors is provided in FIGS. 5-7. In FIG. 5, the same enclosure 302 is shown as in FIGS. 3 and 4, with the hinge 304, the pivoting shaft 306, and the doors 308, 310. As in FIG. 3, the doors 308, 310 are shown in an open position. However, additional columnar supports 311, 312, 313, and 314 are displayed relative to the hinge and the doors. Such columnar supports are optional and can serve to provide a limitation on the amount each individual rotating arm of the hinge (and its associated door) can move relative to the other rotating arm (and its associated door). As a non-limiting example, one or more of the columnar supports 311, 312, 313, and 314 restrict the movement of door 308 such that the door cannot move into a position occupied by open door 310. Thus, it should be appreciated that one or more of the columnar supports restrict the degrees of freedom of movement of one door relative to the other.

FIG. 6 displays the same enclosure 302 as shown previously herein, along with the hinge 304, the pivoting shaft 306, and the doors 308, 310. Also shown are the four columnar supports 311, 312, 313, and 314 shown in FIG. 5. However, in FIG. 6, the doors 308 and 310 are shown in a position between open and closed; that is, the doors have moved towards each other such that the angle between them is less than 180 degrees. As mentioned above herein, such movement is achieved via the two rotating arms (not shown) of hinge 304 moving the doors.

FIG. 7 displays the same enclosure 302 as shown previously herein, along with the hinge 304, the pivoting shaft 306, and the doors 308, 310. Also shown are the four columnar supports 311, 312, 313, and 314 shown in FIGS. 5-6. However, in FIG. 6, the doors 308 and 310 are shown in a fully closed position. The doors have moved towards each other such that the angle between them is the minimum amount allowed due to the shape of the doors. The doors 308 and 310 cannot move further towards each other since portions of door 308 physically contact portions of door 310. Specifically, portion 307 of door 308 is physically contacting portion 309 of door 310, thereby inhibiting the doors from moving closer towards each other.

Although both doors are shown in a closed position, it should be appreciated that even if only one door were moved towards a closed position, one or more of the columnar supports 311, 312, 313, and 314 extend through the hinge such that the door cannot move past a certain point. As a non-limiting example, if door 308 were moved towards the closed position while door 310 retained its position as in FIG. 5, one or more of the columnar supports would physically prevent door 308 from moving past the closed position depicted in FIG. 7. A skilled artisan will appreciate that this restriction prevents door 308 from moving further towards door 310 and possibly overlapping and/or striking door 310 if door 310 were in an open position.

Figure 8:
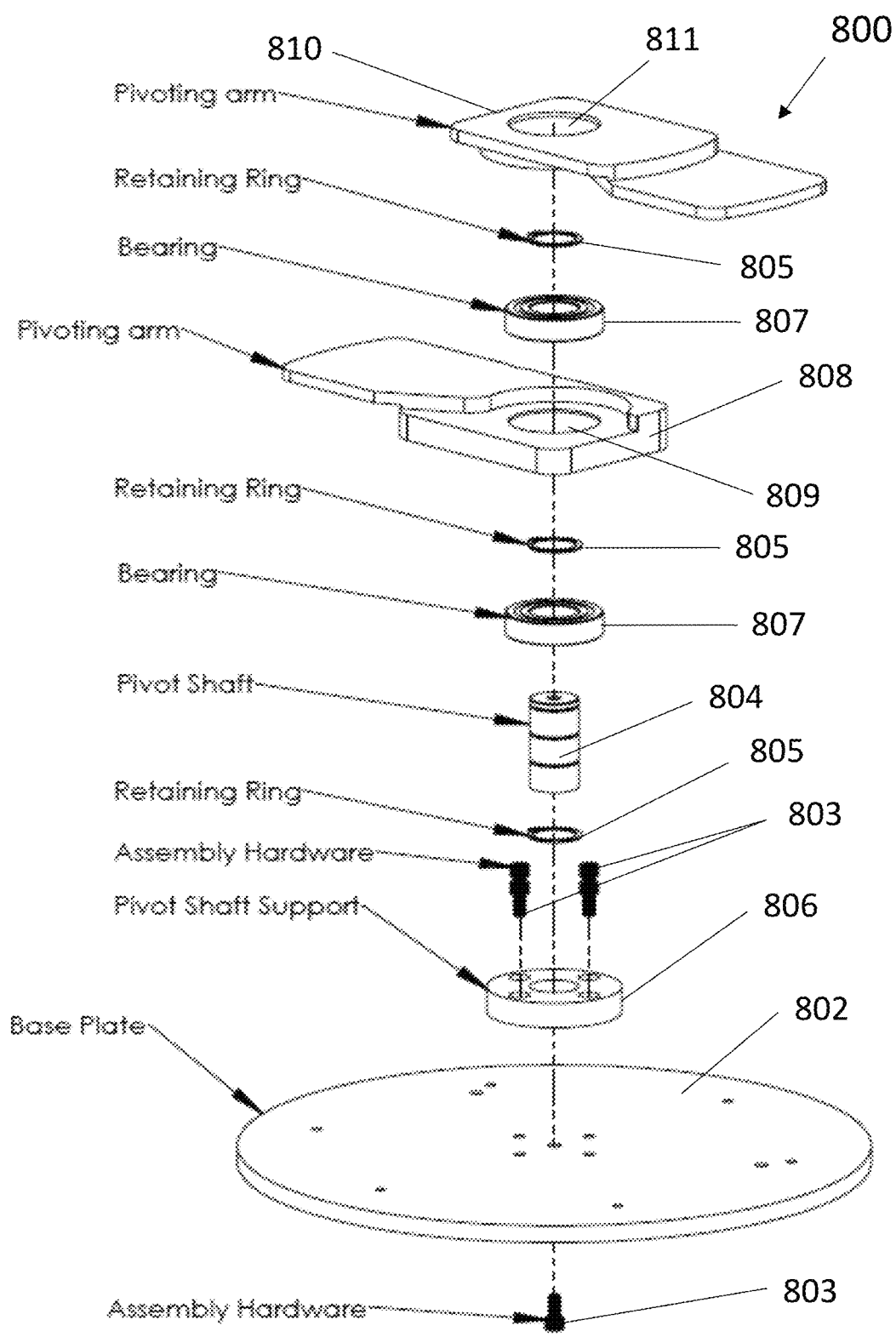
FIG. 8 is a diagram of a top-down perspective view of a hinge, according to an example embodiment.
Figure 9:
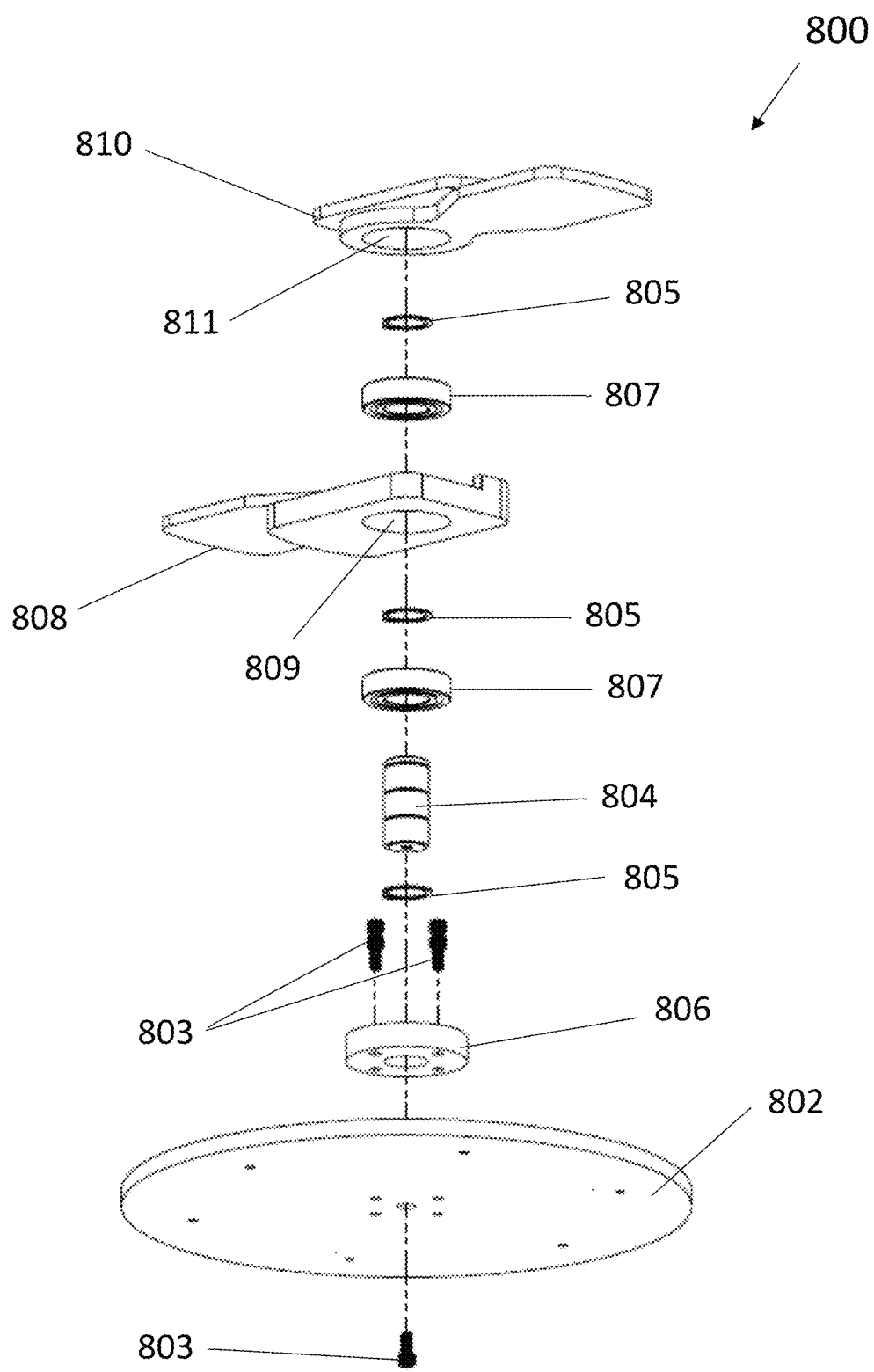
FIG. 9 is a diagram of a bottom-up perspective view of a hinge, according to an example embodiment.

Turning now to FIGS. 8-9, an embodiment of the hinge 800 is shown in either a top-down perspective view (FIG. 8) or a bottom-up perspective view (FIG. 9). The hinge comprises a base plate 802, which is affixed to an enclosure (e.g., a float pod), via assembly hardware 803. It should be appreciated that the term "assembly hardware" herein may include, for instance, screws, pins, and/or any other common attachment mechanisms known in the art. A central pivoting shaft 804 is attached to the base plate 802 via a shaft support 806. Additional assembly hardware 803 is used to affix the shaft support 806 to the base plate 802. Retaining ring 805 provides further securing and/or sealing of shaft 804 to the shaft support 806.

Pivoting arm 808 fits over the pivoting shaft 804 and is rotatable around the shaft with the aid of bearing 807. Additionally, a retaining ring 805 is provided to secure and/or seal the pivoting arm 808 on the shaft 804. As can be seen, pivoting arm 808 fits over the pivoting shaft 804 such that this shaft extends through a hole 809 in the pivoting arm. Similarly, pivoting arm 810 fits over the shaft 804 and vertically above pivoting arm 808. As with pivoting arm 808, pivoting arm 810 is rotatable around the shaft with the aid of bearing 807, and pivoting arm 810 is secured and/or sealed to the shaft 804 via a retaining ring 805. Pivoting arm 810 fits over the pivoting shaft 804 such that this shaft extends through a hole 811 in the pivoting arm. Thus, the pivoting arms 808, 810 are pivotable around the central pivoting shaft 804 in a horizontal plane, and with respect to the base plate 802.

Figure 10:
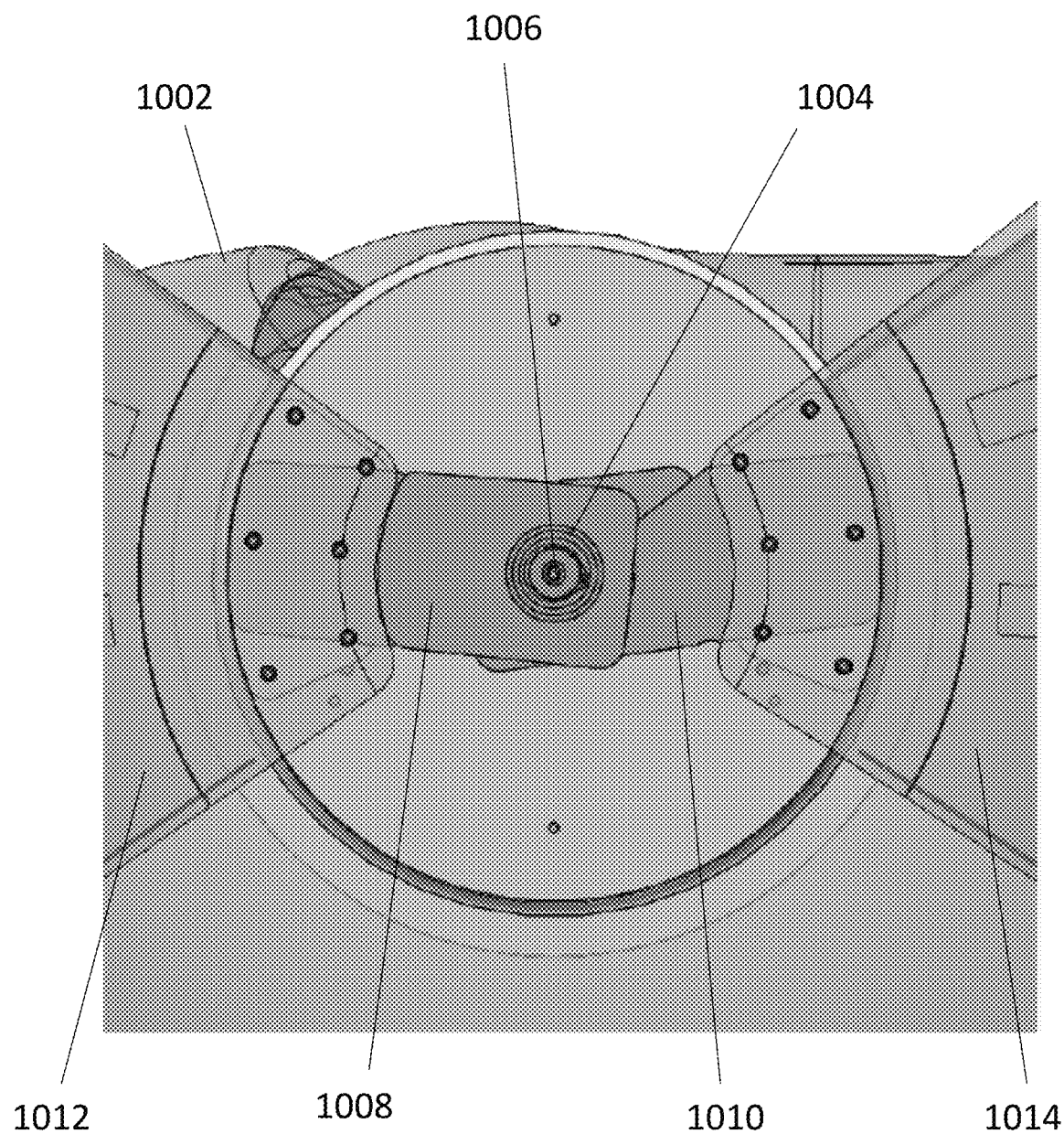
FIG. 10 is a drawing of a top-down view of a hinge operable to move two doors of an enclosure, according to an example embodiment.

Turning now to FIG. 10, an embodiment of the hinge is shown with attached doors. Specifically, a hinge 1004 is affixed to an enclosure 1002. The hinge 1004 comprises a pivoting shaft 1006, as well as two pivoting arms 1008 and 1010. Each of the pivoting arms is affixed to a respective door. Thus, pivoting arm 1008 is affixed to door 1012, and pivoting arm 1010 is affixed to door 1014. A skilled artisan will appreciate that the mechanisms for attaching the pivoting arms to the doors are known in the art and can include, for instance, screws, pins, and the like. Thus, movement and rotation of either one, or both, of pivoting arms 1008 and 1010 about the central shaft 1006 moves one or more of the respective doors 1012 and 1014.

Figure 11:
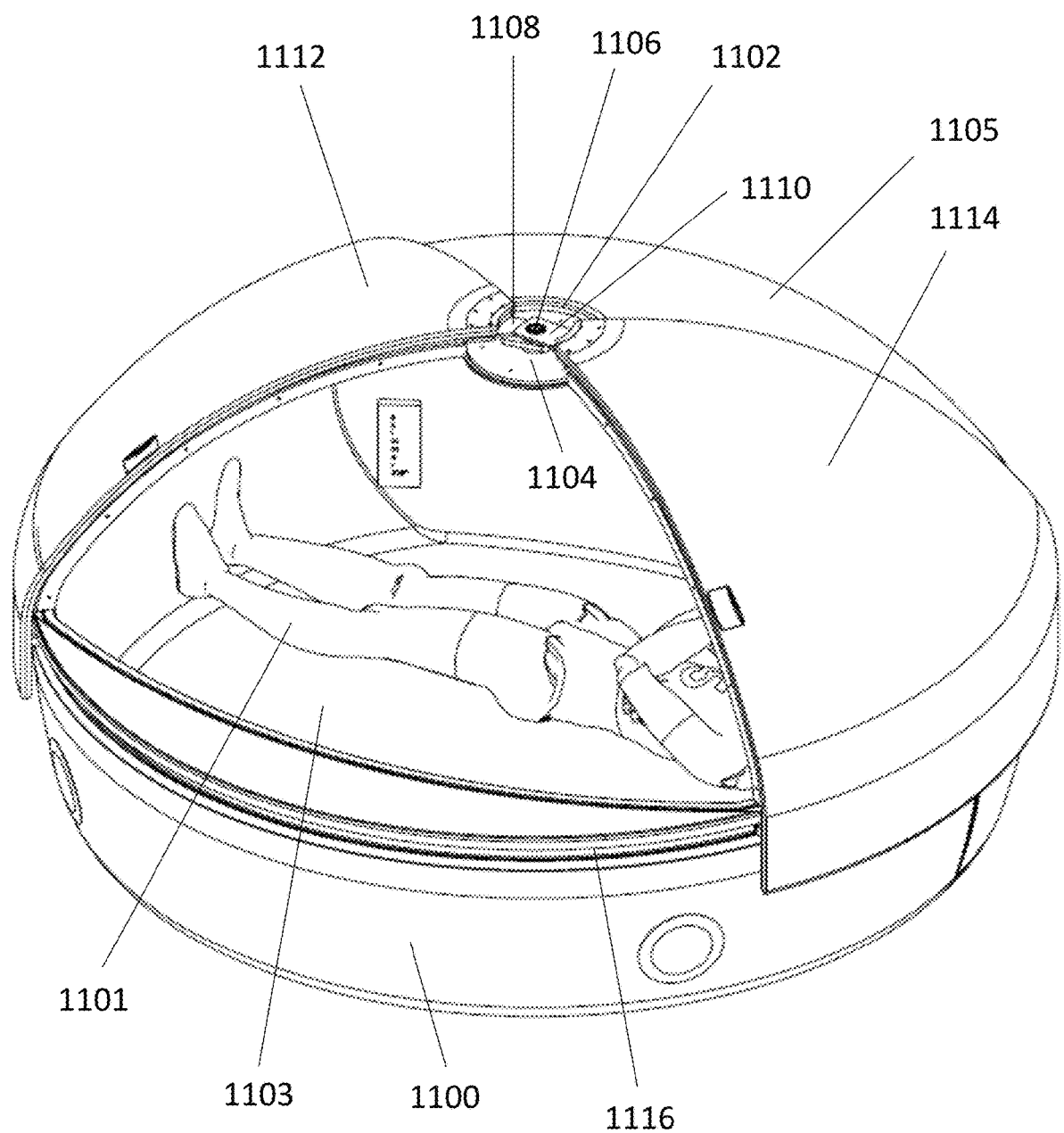
FIG. 11 is a schematic diagram of a perspective view of a hinge connected to, and operable to move, two doors of an enclosure, with the doors in an open position, according to an example embodiment.

As stated above herein, embodiments of the hinge may be attached to an enclosure such as a float pod so that one or more doors on the float pod, which may be curved, are able to open laterally, as opposed to opening vertically like a trapdoor. FIG. 11 is a schematic diagram of a float pod 1100 with a hemispherical or domed roof 1105 having an opening 1103 through which a user 1101 can enter or exit the float pod. The pod comprises two curved doors 1112 and 1114 that are movable from an open position in which the opening 1103 is accessible (illustrated in FIG. 11) to a closed position in which the doors 1112 and 1114 contact each other, thereby shutting off the opening 1103 from the outside environment. It should be appreciated that, when the doors are in a closed position, the interior of the float pod 1100 is sufficiently dark such that the user 1101 can be exposed to the reduced sensory, dark environment inside the pod.

The float pod comprises a hinge 1102 that has been affixed to the roof 1105 of the pod. The hinge comprises a base plate 1104, and a central pivoting shaft 1106 connected to that base plate. Two pivoting arms 1108 and 1110 are attached to, and rotate around, the pivoting shaft 1106. One door is affixed to each of the two pivoting arms. Specifically, door 1112 is attached to, and moves with, pivoting arm 1108, while door 1114 is attached to, and moves with, pivoting arm 1110.

Thus, when the doors 1112 and 1114 are in an open position, such as that depicted in FIG. 11, an opening into the float pod 1100 is revealed such that a user 1101 may enter or leave the float pod. In this open position, the doors 1112 and 1114 may have a maximum angle between them of 180 degrees and rest on top of portions of the roof 1105.

It should be appreciated that the doors 1112 and 1114 may slide open and closed using any manner known in the art, including, for instance, sliding along a circular channel 1116. It should further be appreciated that such a channel may have built-in stops (not shown), which are known in the art, that prevent further opening of the doors beyond a pre-determined point. For instance, these built-in stops may prevent the doors 1112 and 1114 from going past a distance at which the angle between them is 180 degrees.

In one or more embodiments of the hinge described herein, one or more components of the hinge may be made of metal (e.g., aluminum, aluminum alloy, steel, etc.). Specifically, at least the pivoting arms may be made of aluminum or aluminum alloy (e.g., 6061 aluminum or, more preferably, 7075 aluminum). The central pivoting shaft (e.g., shafts 104, 204, 306, 804, 1006, and 1106) may be made of steel to avoid bending of the shaft, and may have a 1-inch diameter.

A skilled artisan will appreciate that the pivoting arms are therefore sturdy enough that they can support, and rotate, doors with a total weight of up to 100 lbs. (e.g., two doors each with a weight of up to 50 lbs.) without bending, mis-aligning, and/or jamming.

It should further be appreciated that at least one embodiment of the hinge described herein permits doors affixed to the pivoting arms of the hinge such that the pivoting arms and/or the attached doors may move laterally up to, and including, a position at which the pivoting arms and/or the attached doors are 180 degrees from each other. Such lateral movement is an improvement upon other hinge and/or door mechanisms, in which, for instance, the doors are locked together and/or must move together. Due to the rotational movement of the two pivoting arms, and the attachment of the doors to those arms, the hinge, in at least one embodiment, avoids the problem of requiring the doors to open to the same point, as well as the use of any cables or cable systems to move the doors apart. Such a hinge therefore is a much simpler and more reliable way to open doors on an enclosure, including doors on a float pod.

These and other objectives and features of the invention are apparent in the disclosure, which includes the above and ongoing written specification.

The foregoing description details certain embodiments of a door hinge. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated.

The invention is not limited to the particular embodiments illustrated in the drawings and described above in detail. Those skilled in the art will recognize that other arrangements could be devised. The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application. While the invention has been described with reference to specific illustrative embodiments, modifications and variations of the invention may be constructed without departing from the spirit and scope of the invention as set forth in the following claims.

We claim:

1. A system for opening and closing doors of an enclosure, said system comprising:
    one or more doors of said enclosure, said one or more doors operable to move from an open position to a closed position, wherein, in said open position, an interior of said enclosure is accessible by a user through an opening, and wherein, in said closed position, said doors cover said opening;
    a door hinge affixed to said enclosure via a base plate, said door hinge comprising a pivoting shaft extending vertically from said base plate, said door hinge comprising one or more rotating arms rotatable around said pivoting shaft, each of said one or more rotating arms being affixed to each of said one or more doors;
    each of said one or more rotating arms has one or more surfaces, wherein said one or more surfaces on a first said one or more rotating arms impacts with said one or more surfaces on a second said one or more rotating arms to limit a maximum angle between said first said one or more rotating arms and said second said one or more rotating arms to one hundred and eighty degrees; and
    wherein rotation of said one or more rotating arms around said pivoting shaft results in movement of said one or more doors from said open position to said closed position.

2. The system of claim 1, wherein said enclosure is a float pod.

3. The system of claim 1, wherein said one or more doors slide laterally away from said opening to said open position, and wherein said one or more doors slide laterally towards said opening to said closed position.

4. The system of claim 1, wherein said pivoting shaft is affixed to said base plate via a shaft support that contacts both said pivoting shaft and said base plate.

5. The system of claim 1, wherein said pivoting shaft is made of steel.

6. The system of claim 1, wherein said one or more rotating arms are made of 7075 aluminum.

7. The system of claim 1, wherein said one or more doors comprise two doors that have a maximum angle therebetween of one hundred and eighty degrees in said open position.

8. The system of claim 7, wherein said one or more rotating arms comprise two rotating arms that are independently rotatable about said pivoting shaft.

9. A door hinge comprising:
    a base plate;
    a shaft support connected to said base plate;
    a pivoting shaft connected to said base plate via said shaft support, said pivoting shaft extending vertically upward from said base plate;
    a first pivoting arm connected to said pivoting shaft and disposed vertically above said shaft support;
    a second pivoting arm connected to said pivoting shaft and disposed vertically above said first pivoting arm;
    wherein said first pivoting arm and said second pivoting arm are both rotatable around said pivoting shaft in a manner that is independent of each other;
    said first pivoting arm has one or more surfaces,
    said second pivoting arm has one or more surfaces,
    wherein said one or more surfaces on said first pivoting arm impact with said one or more surfaces on a said second pivoting arm to limit a maximum angle between said first pivoting arm and said second pivoting arm to one hundred and eighty degrees; and
    wherein a first door is connected to said first pivoting arm, and wherein a second door is connected to said second pivoting arm.

10. The door hinge of claim 9, wherein rotation of said first pivoting arm around said pivoting shaft results in sliding of said first door either away from or towards said second door, and wherein rotation of said second pivoting arm around said pivoting shaft results in sliding of said second door either away from or towards said first door.

11. The door hinge of claim 10, wherein a maximum angle between said first door and said second door is one hundred and eighty degrees.

12. The door hinge of claim 11, wherein said first door and said second door are located on a float pod.

13. The door hinge of claim 12, wherein said pivoting shaft is made of steel.

14. The door hinge of claim 13, wherein said first pivoting arm and said second pivoting arm are each made of 7075 aluminum.

* * * * *